United States Patent [19]

Williams, Jr.

[11] Patent Number: 4,537,184

[45] Date of Patent: Aug. 27, 1985

[54] PORTABLE ORTHOPAEDIC SPLINT SYSTEM

[76] Inventor: James T. Williams, Jr., 4316 Marina City Dr., Apartment No. 633, Marina Del Rey, Calif. 90291

[21] Appl. No.: 536,342

[22] Filed: Sep. 27, 1983

[51] Int. Cl.³ .............................................. A61F 13/04
[52] U.S. Cl. .................................. 128/90; 128/91 R; 128/399; 128/402
[58] Field of Search ............... 128/90, 91 R, 399, 402, 128/403

[56] References Cited

U.S. PATENT DOCUMENTS

| | | | |
|---|---|---|---|
| 1,351,441 | 8/1920 | Pond | 128/91 R |
| 2,958,325 | 11/1960 | Claydon et al. | 128/90 |
| 3,375,822 | 4/1968 | Rose | 128/90 |
| 3,674,021 | 7/1972 | Snyder et al. | 128/90 |
| 3,717,145 | 2/1973 | Berndt et al. | 128/402 |
| 4,060,075 | 11/1977 | Blomer et al. | 128/90 |
| 4,131,114 | 12/1978 | Kirkpatrick | 128/90 |
| 4,397,315 | 8/1983 | Patel | 128/402 |
| 4,454,874 | 6/1984 | Monnier | 128/91 R |

*Primary Examiner*—Stephen C. Pellegrino
*Assistant Examiner*—Mark D. Rooney

[57] ABSTRACT

The invention is a portable orthopaedic splint system comprising a durable tear resistant outer bag containing a linear segment of an orthopaedic splint material impregnated with an unreacted hardening agent, and an inner bag containing a liquid for reacting with said hardening agent to produce a hard stiff splint. The inner bag is capable of being ruptured by manual pressure upon the outer bag and is in juxtaposition with the splint material so that when the outer bag is manually squeezed to rupture the inner bag, the liquid from the inner bag will be released, mixed with said material, and react with the hardening agent therein to form a hard stiff splint which can be used to protect and immobilize the injured member to which it is applied.

5 Claims, 5 Drawing Figures

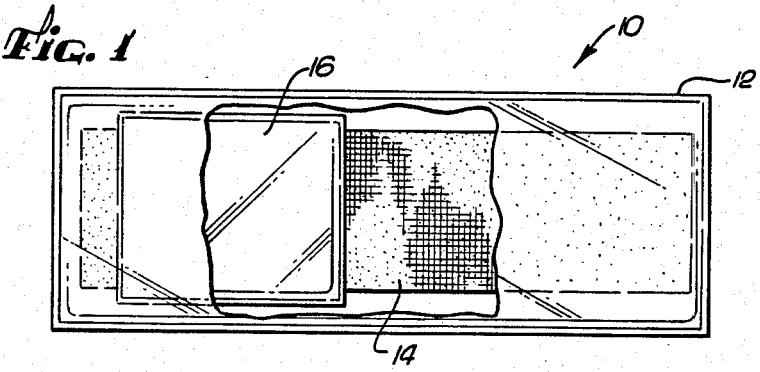
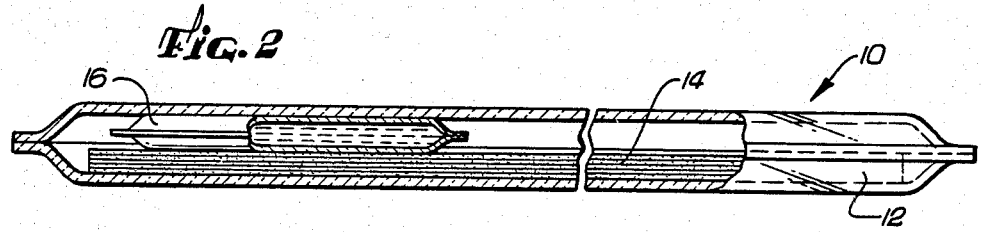
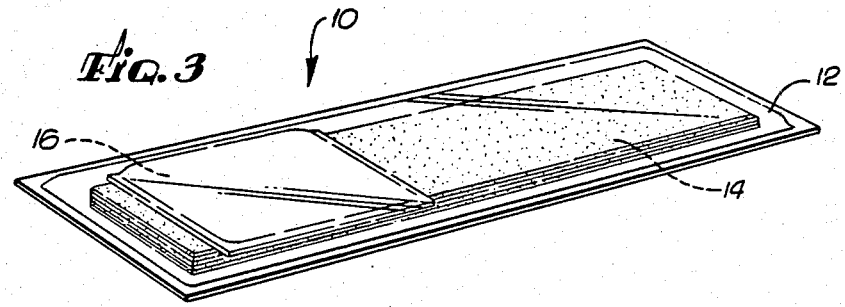
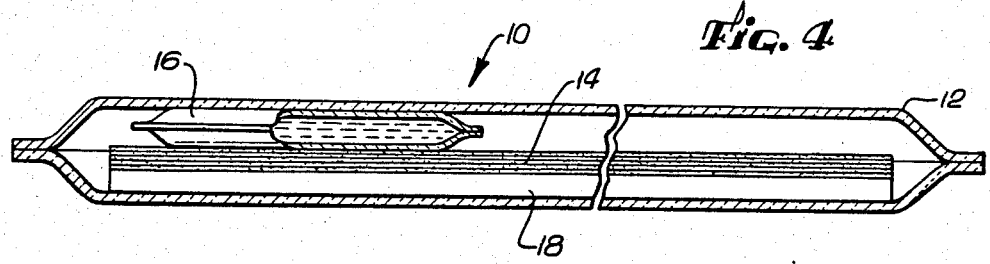
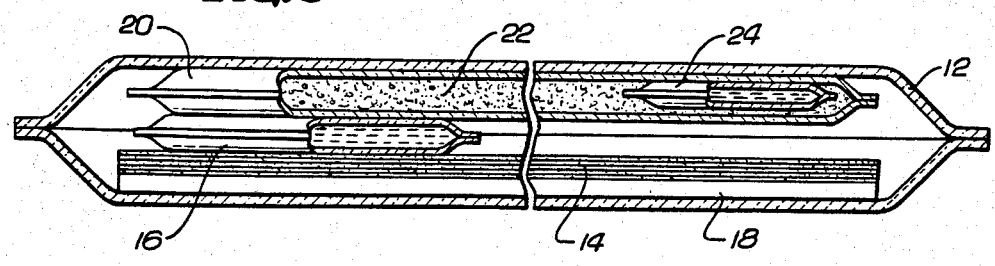

PORTABLE ORTHOPAEDIC SPLINT SYSTEM

BACKGROUND OF THE INVENTION

The need for providing emergency medical treatment at the site of accidents involving fractures and sprains has led to the development of a number of portable casts or splints for such treatment. Such casts or splints, however, have suffered from a number of disadvantages. When such a cast or splint is made from conventional plaster cast material such as disclosed in U.S. Pat. No. 3,900,024, they may be too messy to handle due to the loose plaster which may fall out of the cast material. In addition, water may not be readily available to mix with and harden the plaster in the cast material. When water is added to such cast and the cast is wrapped around the injured area, the cast may not allow for subsequent swelling and may produce circulatory problems.

Other splints, such as those described in U.S. Pat. No. 3,695,258 or in Canadian Pat. No. 638,812, are relatively complicated in their structure and method of application. A complicated splint is particularly disadvantageous because it may not be applied properly during the excitement of rendering emergency medical aid which may be administered by personnel having minimal medical skills.

Other portable casts, such as disclosed in U.S. Pat. No. 4,153,052, use a roll of orthopaedic tape impregnated with a liquid resin which will harden upon exposure to air. Such tape, however, is uncomfortable to work with because it is sticky to the touch, and is very flimsy and will not produce a firm cast unless wrapped around the injured area repeatedly without any allowance being made for swelling which may cause circulatory problems.

It is therefore an object of the present invention to overcome the disadvantages of the aforesaid prior art splint systems. A further object of the present invention is to produce a portable splint system that is relatively inexpensive and simple to manufacture and that is relatively simple to use by personnel having little or no medical training.

SUMMARY OF THE INVENTION

The portable orthopaedic splint system of the present invention comprises a durable tear resistant outer bag containing a linear segment of an orthopaedic splint material impregnated with an unreacted hardening agent, and an inner bag containing a liquid for reacting with said hardening agent to produce a hard stiff splint. The inner bag is capable of being ruptured when manual pressure is exerted upon the outer bag to allow liquid for the inner bag to be released and be absorbed by said splint material. The splint material is manually kneaded to uniformally work in the liquid which will thereafter react with the hardening agent to form a hard stiff splint. The splint is thereafter applied to the fracture or sprain by means of an ace bandage or the like.

The splint system of the present invention may also be provided with a cushion on one side of the splint material to make it more comfortable to the wearer and to provide some insulation against any heat generated by the reaction between the hardening agent and said liquid. A refrigeration bag may also be provided in juxtaposition with the linear splint material to further minimize the heat generated by said reaction and to produce a splint system that will cool and reduce any swelling in the injured area to which it is applied.

BRIEF DESCRIPTION OF THE DRAWINGS

The portable orthopaedic splint system of the present invention will now be described in reference to the following drawings in which:

FIG. 1 is a top view of a first embodiment of said splint system;

FIG. 2 is an elevational view of said first embodiment;

FIG. 3 is a perspective view of said embodiment;

FIG. 4 is an elevational view of a second embodiment of said splint system;

FIG. 5 is an elevational view of a third embodiment of said splint system.

DETAILED DESCRIPTION OF THE INVENTION

The outer bag 12 used with the portable orthopaedic splint system 10 of the present invention shown in FIGS. 1–3, is made from a tough durable tear resistant material that will not tear or rip during rough handling, such as polyethylene or the like.

The splint material 14 inside the outer bag is made from a conventional orthopaedic cotton gauze or other like material which will absorb the liquid used for reacting with the hardening agent. The splint material is impregnated with an unreacted hardening agent such as plaster or an unreacted hardenable resin such as epoxy resin, polyurethane, polypropylene trimethylol propane, or other well known resins that will harden upon admixture with an activating agent. It is also preferable to select a hardening agent that will not produce excessive amounts of heat upon reaction to minimize the risk of skin burns and to minimize any aggravation of the swelling which generally accompanies fractures or sprains.

The inner bag 16 containing a liquid for reacting with the hardening agent should be strong enough to withstand rough handling but weak enough so it may be ruptured when manually squeezed through the outer bag 12 within which it is contained. The material for the inner bag may be made from a conventional plastic film or a paper product which meets this requirement.

The liquid in the inner bag is selected for its ability to react with the hardening agent. When the hardening agent is plaster, the liquid is water. When the hardening agent is one of the aforesaid resins, the liquid is one of the corresponding activating agents known to react with said resin to produce a hard product.

A cushion 18 made of a foamed plastic material or the like as illustrated in FIG. 4, may be provided on one side of the splint material or on the outside of the outer bag 12 to provide some cushioning when the splint system is applied to the injured member, and to provide some insulation to protect the member from skin burns or from heat released during the reaction between the hardening agent and the activating liquid.

The splint material 14 is provided as a linear segment so it is ready for use and need not be unwound from a roll. Providing the splint material as a linear segment also allows the splint material to be manufactured having a substantial thickness so that when it is reacted to form a stiff firm splint, it will be of sufficient thickness to provide the firmness and strength necessary to function as a splint.

The orthopaedic splint system of the present invention may also be provided with a refrigeration bag 20 in juxtaposition with the linear splint material, as shown in FIG. 5, to reduce any heat generated from the reaction between the hardening agent and the liquid for reacting therewith. The refrigeration bag 20 may be in direct contact with the linear splint material, as shown in FIG. 5, or may be secured on the outside of the outer bag 12.

The refrigeration bag 20 will also provide cooling for the injured member and reduce any swelling therein. The refrigeration bag comprises a durable tear resistant outer bag containing a water reactive refrigeration agent 22 and an inner bag containing water 24. The inner bag is capable of being ruptured by manual pressure to release the water which will react with the refrigeration agent 22 to produce the desired cooling effect. The refrigeration agent may be selected from any one of a number of chemicals well known to have a cooling effect upon admixture with water, such as ammonium nitrate, calcium chloride, sodium sulfate, sodium carbonate (hydrated), ammonium chloride, potassium iodide or urea.

While the embodiments of the invention set forth herein for purposes of disclosure are considered to be preferred, it is to be understood that this invention is intended to cover all changes and modifications in the disclosed embodiments which fall within the spirit and scope of the invention.

What is claimed is:

1. A portable orthopaedic splint system, comprising:
   a durable tear-resistant outer bag containing a linear segment of an orthopaedic splint material impregnated with an unreacted hardening agent;
   an inner bag containing a liquid for reacting with said hardening agent to produce a hard, stiff splint, said inner bag capable of being ruptured by manual pressure upon said outer bag and being in juxtaposition with said splint material, whereby when said outer bag is manually squeezed to rupture said inner bag, the liquid from said inner bag will be released, mix with said splint material, and react with the hardening agent therein to form a hard, stiff splint; and
   a refrigeration bag in juxtaposition with said linear splint material, said refrigeration bag comprising a durable tear-resistant outer refrigeration bag containing a water reactive refrigeration agent and an inner refrigeration bag containing water, said inner refrigeration bag capable of being ruptured by manual pressure to release said water for reaction with said refrigeration agent to produce a cooling effect in said splint system and thereby counteract any heat released from the reaction of said hardening agent and reduce any swelling in the injured area to which the splint system is applied.

2. The portable orthopaedic splint system of claim 1 wherein said splint material is conventional plaster cast material impregnated with plaster and wherein the liquid in said inner bag is water.

3. The portable orthopaedic splint system of claim 1 wherein said splint material is impregnated with a resin hardener and wherein the liquid in said inner bag comprises an activating agent to harden said resin when admixed therewith.

4. The portable orthopaedic splint system of claim 1 having a cushion on one side of said splint material, for application to the injured area to be protected and immobilized.

5. The portable orthopaedic splint system of claim 1 wherein said splint material is conventional plaster cast material impregnated with plaster and wherein the liquid in said inner bag is water, said refrigeration bag containing a refrigeration agent which will be activated by the water contained within said inner refrigeration bag to release said water, thus producing a cooling effect.

* * * * *